United States Patent
Amakawa et al.

(10) Patent No.: US 7,119,230 B2
(45) Date of Patent: Oct. 10, 2006

(54) PROCESS FOR PRODUCTION OF XYLYLENEDIAMINE AND/OR CYANOBENZYLAMINE

(75) Inventors: Kazuhiko Amakawa, Niigata (JP); Takuji Shitara, Niigata (JP)

(73) Assignee: Mitsubishi Gas Chemical Co., Inc., Tokyo (JP)

( * ) Notice: Subject to any disclaimer, the term of this patent is extended or adjusted under 35 U.S.C. 154(b) by 539 days.

(21) Appl. No.: 10/608,071

(22) Filed: Jun. 30, 2003

(65) Prior Publication Data

US 2004/0002614 A1 Jan. 1, 2004

(30) Foreign Application Priority Data

Jul. 1, 2002 (JP) .............................. 2002-192157

(51) Int. Cl.
*C07C 209/48* (2006.01)
(52) U.S. Cl. ...................................... 564/385; 564/415
(58) Field of Classification Search ..................... None
See application file for complete search history.

(56) References Cited

U.S. PATENT DOCUMENTS 6,476,267 B1 11/2002 Fuchigami et al.

FOREIGN PATENT DOCUMENTS

| DE | 75 074 | 8/1970 |
|---|---|---|
| DE | 77 983 | 12/1970 |
| DE | 17 68 796 | 1/1972 |
| EP | 1 193 244 | 4/2002 |
| EP | 1 193 247 | 4/2002 |
| EP | 1 279 661 | 1/2003 |
| GB | 814631 | 6/1959 |
| GB | 821404 | 10/1959 |
| WO | WO 00/46179 | 8/2000 |

OTHER PUBLICATIONS

Communication and European Search Report mailed Aug. 12, 2004, for No. EP 03 01 3772.*

* cited by examiner

*Primary Examiner*—Brian Davis
(74) *Attorney, Agent, or Firm*—Antonelli, Terry, Stout and Kraus, LLP.

(57) ABSTRACT

In the process of the present invention, xylylenediamine and/or cyanobenzylamine is produced by a catalytic liquid-phase hydrogenation of a phthalonitrile compound. The liquid-phase hydrogenation is performed by controlling the concentration of a benzamide compound to a specific level or lower. In a preferred embodiment, the concentration of a benzoic acid compound is further controlled to a specific level or lower. By the process, xylylenediamine and/or cyanobenzylamine is produced at high yields and the catalyst life is prolonged.

10 Claims, No Drawings

PROCESS FOR PRODUCTION OF XYLYLENEDIAMINE AND/OR CYANOBENZYLAMINE

BACKGROUND OF THE INVENTION

1. Field of the Invention

The present invention relates to a process for producing a xylylenediamine and/or a cyanobenzylamine by hydrogenation of a phthalonitrile compound (dicyanobenzene compound). The xylylenediamine is useful as a raw material for polyamide resins, curing agents, etc., as well as an intermediate material for isocyanate resins, etc. The cyanobenzylamine is useful as a raw material and an intermediate material for medicines, agricultural chemicals, polymer additives and other organic compounds.

2. Description of the Prior Art

It is well known in the art to produce the xylylenediamine by hydrogenating the phthalonitrile compound in a liquid phase in the presence of a catalyst.

For example, Japanese Patent Publication No. 38-8719 discloses a batch-wise hydrogenation of the phthalonitrile compound in an autoclave. The proposed hydrogenation is conducted in an alcoholic solvent in the presence of a very small amount of a caustic alkali agent as well as Raney nickel or Raney cobalt to produce the corresponding diamine. Japanese Patent Application Laid-Open No. 54-41804 discloses another batch-wise hydrogenation of the phthalonitrile compound in an autoclave. The proposed hydrogenation is conducted in a mixed solvent of a lower alcohol and a cyclic hydrocarbon in the presence of a hydroxide or an alcoholate of alkali metal or alkali earth metal, and a Raney nickel or Raney cobalt-containing catalyst to produce the corresponding diamine. Japanese Patent Application Laid-Open No. 6-121929 discloses a batch-wise hydrogenation of isophthalonitrile in an autoclave. The proposed hydrogenation is conducted in a mixed solvent of methanol and ammonia in the presence of a Rh/Co-containing catalyst to produce the corresponding diamine. Japanese Patent Publication No. 53-20969 discloses a catalytic reduction of the phthalonitrile compound with hydrogen in a liquid phase in the presence of a Ni/Cu/Mo-containing catalyst, for example, by a fixed bed continuous hydrogenation. "PROCESS HANDBOOK (1978)" edited by Japan Petroleum Society discloses an industrial process for the production of xylylenediamine in which a raw nitrile is introduced into a hydrogenation reactor together with a solvent and a catalyst to subject the nitrile to hydrogenation reaction under a slurried condition. Japanese Patent Application Laid-Open No. 2002-105035 discloses a process for producing xylylenediamine in which the phthalonitrile compound obtained by ammoxidation of xylene is absorbed into an organic solvent by contacting, and liquid ammonia is added to the resultant solution to hydrogenate the phthalonitrile compound without separating the phthalonitrile compound.

The production of cyanobenzylamine by hydrogenating the phthalonitrile compound in a liquid phase in the presence of a catalyst is disclosed in Japanese Patent Application Laid-Open Nos. 49-85041, 6-507909, 9-40630 and 10-204048, etc.

The phthalonitrile compound used as a starting material for xylylenediamine or cyanobenzylamine is produced by various methods such as the ammoxidation of an alkylated benzene such as xylene, the reaction between a dichlorobenzene and hydrogen cyanide, and the reaction between a phthalic acid compound and ammonia. Of these methods, the ammoxidation of the alkylated benzene is industrially preferred. The ammoxidation of xylene is performed by known methods in the presence of known catalysts as disclosed in Japanese Patent Publication No. 49-45860, Japanese Patent Application Laid-open Nos. 49-13141, 63-190646, 5-170724, 1-275551 and 9-71561, etc.

SUMMARY OF THE INVENTION

In the course of study on the production of xylylenediamine and/or cyanobenzylamine by the hydrogenation of the phthalonitrile compound, the present inventors have found that the above conventional methods unfavorably cause significant changes in the yield and the catalyst life depending upon raw material used and reaction conditions.

Therefore, an object of the present invention is to provide a process for stably and economically producing, at high yields with prolonged catalyst life, xylylenediamine and/or cyanobenzylamine by the hydrogenation of the phthalonitrile compound.

As a result of extensive study in view of the above object, the inventors have found that a benzamide compound contained in a reaction solution for the hydrogenation of the phthalonitrile compound has a considerable influence on the yield and the catalyst life, and that the above object is achieved by controlling the concentration thereof to a specific level or lower. The inventors have further found that the above object can be achieve more effectively by further controlling the concentration a benzoic acid compound in the reaction solution to a specific level or lower. The present invention has been accomplished on the basis of these findings.

Thus, the present invention provides a process for producing xylylenediamine and/or cyanobenzylamine by a liquid-phase hydrogenation of a phthalonitrile compound in the presence of a catalyst, the liquid-phase hydrogenation being performed while controlling a concentration of a benzamide compound in a reaction solution to 0.35% by weight or lower.

More preferred results can be obtained when the hydrogenation is performed while further controlling a concentration of a benzoic acid compound in the reaction solution to 0.1% by weight or lower.

DETAILED DESCRIPTION OF THE INVENTION

The present invention will be described in detail below.

The phthalonitrile compound (dicyanobenzene compound) used in the present invention is a compound having two nitrile groups on the benzene ring, such as isophthalonitrile and terephthalonitrile. The benzene ring of the phthalonitrile compound may also have, in addition to the two nitrile groups, another substituent, e.g., halogen atom such as fluorine and chlorine, alkyl group such as methyl and ethyl, and alkoxyl group such as methoxyl and ethoxyl. Examples of the substituted phthalonitrile compound include 2-chloroterephthalonitrile, 5-methylisophthalonitrile and 4-methylisophehalonitrile. These phthalonitrile compounds are hydrogenated to the corresponding xylylenediamines and/or cyanobenzylamines.

In the present invention, the hydrogenation reaction is conducted in a liquid phase, preferably using a solvent that is stable under the hydrogenation conditions. Examples of the solvent include hydrocarbons such as toluene, xylene and trimethylbenzene; ethers such as tetrahydrofuran and dioxane; lower aliphatic amides such as dimethylformamide and dimethylacetamide; alcohols such as methanol, ethanol and propanol; and ammonia. These solvents may be used singly or in combination of two or more. Since the yields are increased in the presence of ammonia, ammonia is preferably used as a part of the solvent. The amount of the solvent is 1 to 99 parts by weight, preferably 1.5 to 99 parts by weight based on one part by weight of the phthalonitrile compound.

The hydrogen gas used for the hydrogenation reaction may contain impurities that take no part in the hydrogenation, such as methane and nitrogen. However, if the content of the impurities is too high, the total reaction pressure must be considerably increased to achieve a necessary hydrogen partial pressure, being industrially disadvantageous. The hydrogen concentration in the gas is preferably 50 mol % or higher.

As the hydrogenation catalyst, there may be used known catalysts such as supported metal catalysts, non-supported metal catalysts, Raney catalysts and noble metal catalysts. Of these catalysts, preferred are catalysts containing nickel, cobalt or palladium. The amount of the catalyst to be used is preferably 0.1 to 200 parts by weight, more preferably 1 to 100 parts by weight based on 100 parts by weight of the phthalonitrile compound for a slurry bed hydrogenation. In a fixed bed hydrogenation, the phthalonitrile compound is supplied preferably 0.1 to 1000 parts by weight/h, more preferably 0.1 to 500 parts by weight/h based 100 parts by weight of the catalyst. When the catalyst amount is less than the above ranges, a sufficient productivity cannot be attained. An amount exceeding the above ranges creates no additional effect, resulting in the increase of catalyst costs.

In the present invention, an additive may be used to accelerate the hydrogenation or improve the yield. Examples of the additives include hydroxides or alcoholates of alkali metals or alkaline earth metals, such as lithium hydroxide, sodium hydroxide and potassium hydroxide.

The hydrogenation may be performed batch-wise or continuously either in fixed bed manner or in slurry bed manner. The hydrogenation temperature is preferably 20 to 200° C., more preferably 30 to 180° C., and the hydrogen pressure in the hydrogenation system is preferably 1 to 30 MPa, more preferably 2 to 20 MPa.

In the present invention, the concentration of the benzamide compound in the reaction solution is controlled to a specific level or lower to suitably perform the liquid-phase hydrogenation.

The concentration of the benzamide compound in the reaction solution is limited to 0.35% by weight or lower. When the concentration of the benzamide compound is higher than 0.35% by weight, the yields of xylylenediamine and/or cyanobenzylamine are considerably lowered. When the concentration of the benzamide compound is reduced to 0.07% by weight or lower, the catalyst is effectively prevented from being deactivated, resulting in a prolonged catalyst life. Particularly, in the industrial production of xylylenediamine and/or cyanobenzylamine, the catalyst life is an extremely important factor, and therefore, the concentration of the benzamide compound is preferably controlled to 0.07% by weight or lower.

In the hydrogenation of the present invention, it is preferred to further control the concentration of the benzoic acid compound in the reaction solution to 0.1% by weight or lower, preferably 0.05% by weight or lower. By limiting the concentration to the above range, the effect of the present invention is more enhanced.

Examples of the benzamide compound include 3-cyanobenzamide, 4-cyanobenzamide, isophthalamide, m-toluamide, p-toluamide and benzamide. Examples of the benzoic acid compound include 3-cyanobenzoic acid, 4-cyanobenzoic acid, 3-methylbenzoic acid, 4-methylbenzoic acid and benzoic acid. The benzoic acid compound referred to herein may include free acid forms and slat forms, for example, alkali metal salts or alkaline earth metal salts such as sodium salts, potassium salts and calcium salts; ammonium salts; and salts with an amine compound such as xylylenediamine and cyanobenzylamine. The benzamide compound and the benzoic acid compound are mainly derived from the starting phthalonitrile compound. Therefore, the effects of the present invention are usually achieved by suitably controlling the contents of the benzamide compounds and the benzoic acid compounds in the starting phthalonitrile compound. In particular, when isophthalonitrile or terephthalonitrile is used as the starting phthalonitrile compound, 3-cyanobenzamide and 4-cyanobenzamide are mainly contained as the benzamide compound, and 3-cyanobenzoic acid and 4-cyanobenzoic acid are mainly contained as the benzoic acid compound. Therefore, the contents are preferably controlled by paying a particular attention to these cyanobenzamides and cyanobenzoic acids.

The contents of the benzamide compounds and the benzoic acid compounds in the starting phthalonitrile compound may be reduced to as low as substantially zero by known purification treatments such as distillation.

The reaction solution referred to herein means a solution that is actually brought into contact with the catalyst in the hydrogenation reactor. More specifically, the reaction solution is a liquid component that is fed to the reactor and is present in the form of liquid in the reactor, i.e., exclusive of gaseous components and the catalyst. In a fixed bed continuous flow reaction or a slurry bed continuous flow reaction, the reaction solution comprises all of the liquid components left after removing the gaseous components such as hydrogen and the catalyst from the components fed to the reactor. The amount thereof is generally expressed by the feed amount per unit time. The reaction solution is generally composed of the starting phthalonitrile compound and the solvent, and an optional additive for accelerating the reaction. In a batch-wise method or a semibatch-wise method, the reaction solution is a total of the liquid components charged into the reactor, and is composed of the starting phthalonitrile compound, the solvent and the optional additive.

In the hydrogenation of the phthalonitrile compound, the selectivity to xylylenediamine or cyanobenzylamine can be controlled by selecting the kind of catalyst and the reaction conditions such as temperature, pressure and reaction time. To selectively produce the cyanobenzylamine from the phthalonitrile compound, a palladium catalyst described in Japanese Patent Application Laid-Open No. 49-85041 can be used.

Xylylenediamine and cyanobenzylamine produced by the hydrogenation may be purified by known methods such as distillation. If both of xylylenediamine and cyanobenzylamine are simultaneously produced, it is usually difficult to separate these compounds by an ordinary distillation because of small difference in their boiling points. Event in the hydrogenation of the phthalonitrile compound intended to produce only cyanobenzylamine, the by-production of xylylenediamine cannot be prevented. Therefore, the xylylenediamine must be removed from the reaction product to obtain a high-purity cyanobenzylamine. The separation of cyanobenzylamine from xylylenediamine is performed by known methods for producing hydrates of cyanobenzylamine as described in British Patent No. 814631, Japanese Patent Application Laid-Open No. 2000-273077, etc.

The present invention will be described in more detail by reference to the following examples. However, it should be noted that the following examples are only illustrative and not intended to limit the invention thereto.

Preparation of Catalyst

Into an aqueous solution of 305.0 g of nickel nitrate hexahydrate ($Ni(NO_3)_2 \cdot 6H_2O$), 6.5 g of copper nitrate trihydrate ($Cu(NO_3)_2 \cdot 3H_2O$) and 7.1 g of chromium nitrate nonahydrate ($Cr(NO_3)_3 \cdot 9H_2O$) in 1 kg of 40° C. pure water, was suspended 29.6 g of diatomaceous earth under stirring at 40° C. Then, an aqueous solution of 128.6 g of sodium carbonate ($Na_2CO_3$) in 1 kg of 40° C. pure water was poured into the suspension under sufficient stirring to prepare a precipitate slurry. The slurry was heated to 80° C. and held at that temperature for 30 min. The precipitate slurry thus treated was filtered to separate the precipitates, which were washed with water. The precipitates were dried at 110° C. over one night, and then calcined in air at 380° C. for 18 h. The calcined powder was mixed with 3% by weight of graphite and made into 3.0 mm φ×2.5 mm tablets by a tablet machine. The tablets were reduced at 400° C. under a hydrogen flow, and then, stabilized by an oxidation treatment over one night at a temperature from room temperature to 40° C. under a flow of dilute oxygen gas (oxygen/nitrogen=1/99 by volume). Then, the tablets were pulverized and classified to have a particle size of 12 to 28 mesh, thereby obtaining a catalyst A.

EXAMPLE 1

A 100-ml autoclave was charged with 4.0 g of the catalyst A previously reduced and activated under a hydrogen flow at 200° C. and 12.8 g of isophthalonitrile containing as impurities 0.12% by weight of 3-cyanobenzamide and 0.01% by weight of 3-cyanobenzoic acid. After further charging 16 g of methanol and 7 g of liquid ammonia, the inner pressure was increased to 20 MPa (gauge) by introducing hydrogen. The concentration in the reaction solution was 0.043% by weight for the benzamide compound and 0.004% by weight for the benzoic acid compound. The autoclave was shaken at 80° C. until the inner pressure was no longer changed. The gas chromatographic analysis showed that the conversion of isophthalonitrile was 99.6 mol % and the yield of m-xylylenediamine was 75.7 mol %. The by-products were substantially high-boiling substances and the yield of 3-cyanobenzylamine was 0.3 mol %.

EXAMPLE 2

The same procedure as in Example 1 was repeated except that 12.8 g of isophthalonitrile containing as impurities 0.84% by weight of 3-cyanobenzamide and 0.01% by weight of 3-cyanobenzoic acid were used as the starting phthalonitrile compound for the hydrogenation. The concentration in the reaction solution was 0.30% by weight for the benzamide compound and 0.004% by weight for the benzoic acid compound. The gas chromatographic analysis showed that the conversion of isophthalonitrile was 99.2 mol % and the yield of m-xylylenediamine was 74.8 mol %. The by-products were substantially high-boiling substances and the yield of 3-cyanobenzylamine was 0.3 mol %.

EXAMPLE 3

The same procedure as in Example 1 was repeated except that 12.8 g of isophthalonitrile containing as impurities 0.12% by weight of 3-cyanobenzamide and 0.12% by weight of 3-cyanobenzoic acid were used as the starting phthalonitrile compound for the hydrogenation. The concentration in the reaction solution was 0.043% by weight for the benzamide compound and 0.043% by weight for the benzoic acid compound. The gas chromatographic analysis showed that the conversion of isophthalonitrile was 99.4 mol % and the yield of m-xylylenediamine was 74.1 mol %. The by-products were substantially high-boiling substances and the yield of 3-cyanobenzylamine was 0.2 mol %.

EXAMPLE 4

The same procedure as in Example 1 was repeated except that 12.8 g of terephthalonitrile containing as impurities 0.14% by weight of 4-cyanobenzamide and 0.01% by weight of 4-cyanobenzoic acid were used as the starting phthalonitrile compound for the hydrogenation. The concentration in the reaction solution was 0.05% by weight for the benzamide compound and 0.004% by weight for the benzoic acid compound. The gas chromatographic analysis showed that the conversion of terephthalonitrile was 99.2 mol % and the yield of p-xylylenediamine was 76.3 mol %. The by-products were substantially high-boiling substances and the yield of 4-cyanobenzylamine was 0.4 mol %.

Comparative Example 1

The same procedure as in Example 1 was repeated except that 12.8 g of isophthalonitrile containing as impurities 2.11% by weight of 3-cyanobenzamide and 0.01% by weight of 3-cyanobenzoic acid were used as the starting phthalonitrile compound for the hydrogenation. The concentration in the reaction solution was 0.75% by weight for the benzamide compound and 0.004% by weight for the benzoic acid compound. The gas chromatographic analysis showed that the conversion of isophthalonitrile was 99.3 mol % and the yield of m-xylylenediamine was 70.2 mol %. The by-products were substantially high-boiling substances and the yield of 3-cyanobenzylamine was 0.5 mol %.

Comparative Example 2

The same procedure as in Example 1 was repeated except that 12.8 g of isophthalonitrile containing as impurities 5.36% by weight of 3-cyanobenzamide and 0.01% by weight of 3-cyanobenzoic acid were used as the starting phthalonitrile compound for the hydrogenation. The concentration in the reaction solution was 1.92% by weight for the benzamide compound and 0.004% by weight for the benzoic acid compound. The gas chromatographic analysis showed that the conversion of isophthalonitrile was 99.1 mol % and the yield of m-xylylenediamine was 69.9 mol %. The by-products were substantially high-boiling substances and the yield of 3-cyanobenzylamine was 0.9 mol %.

Comparative Example 3

The same procedure as in Example 1 was repeated except that 12.8 g of isophthalonitrile containing as impurities 3.42% by weight of 3-cyanobenzamide and 0.24% by weight of 3-cyanobenzoic acid were used as the starting phthalonitrile compound for the hydrogenation. The concentration in the reaction solution was 1.22% by weight for the benzamide compound and 0.086% by weight for the benzoic acid compound. The gas chromatographic analysis showed that the conversion of isophthalonitrile was 99.2 mol % and the yield of m-xylylenediamine was 64.3 mol %. The by-products were substantially high-boiling substances and the yield of 3-cyanobenzylamine was 0.7 mol % or lower.

Comparative Example 4

The same procedure as in Example 1 was repeated except that 12.8 g of terephthalonitrile containing as impurities 3.36% by weight of 4-cyanobenzamide and 0.20% by weight of 4-cyanobenzoic acid were used as the starting phthalonitrile compound for the hydrogenation. The concentration in the reaction solution was 1.20% by weight for the benzamide compound and 0.072% by weight for the benzoic acid compound. The gas chromatographic analysis showed that the conversion of terephthalonitrile was 99.2 mol % and the yield of p-xylylenediamine was 64.1 mol %. The by-products were substantially high-boiling substances and the yield of 4-cyanobenzylamine was 0.6 mol %.

EXAMPLE 5

A tube reactor having an inner diameter of 10 mm was packed with 33 g of the catalyst A (packing height: 420 mm). After reductively activating the catalyst A under a hydrogen flow at 200° C., a mixed solution comprising isophthalonitrile containing as impurities 0.11% by weight of 3-cyanobenzamide and 0.01% by weight of 3-cyanobenzoic acid (crude IPN), m-xylene (MX) and ammonia (NH$_3$) (crude IPN:MX:NH$_3$=1:2:7 by weight) was introduced into the tube reactor from a top thereof at a feed rate of 55 g/hr. Separately, a hydrogen gas was introduced under pressure into the reactor to keep the reaction pressure at 15 MPa, thereby continuously performing the hydrogenation. The concentration in the reaction solution was 0.011% by weight for the benzamide compound and 0.001% by weight for the benzoic acid compound. The reaction temperature was maintained at 75° C., and the reaction product solution taken out of the reactor was analyzed by gas chromatography, showing that the yield of m-xylylenediamine was 90.9 mol %.

The reaction was continued by raising only the temperature so as to keep the above yield of m-xylylenediamine, thereby evaluating, the catalyst life by the number of days taken until the temperature for keeping the yield reached 90° C. After 21 days, the reaction temperature reached 90° C.

EXAMPLE 6

The same procedure as in Example 5 was repeated except for using isophthalonitrile containing as impurities 0.63% by weight of 3-cyanobenzamide and 0.01% by weight of 3-cyanobenzoic acid as the starting phthalonitrile compound for the hydrogenation. The concentration in the reaction solution was 0.063% by weight for the benzamide compound and 0.001% by weight for the benzoic acid compound. The reaction temperature was maintained at 75° C., and the reaction product solution taken out of the reactor was analyzed by gas chromatography, showing that the yield of m-xylylenediamine was 89.4 mol %.

The reaction was continued by raising only the temperature so as to keep the above yield of m-xylylenediamine, thereby evaluating the catalyst life by the number of days taken until the reaction temperature for keeping the yield reached 90° C. After 18 days, the reaction temperature reached 90° C.

EXAMPLE 7

The same procedure as in Example 5 was repeated except for using isophthalonitrile containing as impurities 0.12% by weight of 3-cyanobenzamide and 0.12% by weight of 3-cyanobenzoic acid as the starting phthalonitrile compound for the hydrogenation. The concentration in the reaction solution was 0.012% by weight for the benzamide compound and 0.012% by weight for the benzoic acid compound. The reaction temperature was maintained at 75° C., and the reaction product solution taken out of the reactor was analyzed by gas chromatography, showing that the yield of m-xylylenediamine was 88.8 mol %.

The reaction was continued by raising only the temperature so as to keep the above yield of m-xylylenediamine, thereby evaluating the catalyst life by the number of days taken until the reaction temperature for keeping the yield reached 90° C. After 17 days, the reaction temperature reached 90° C.

EXAMPLE 8

The same procedure as in Example 5 was repeated except for using isophthalonitrile containing as impurities 1.14% by weight of 3-cyanobenzamide and 0.02% by weight of 3-cyanobenzoic acid as the starting phthalonitrile compound for the hydrogenation. The concentration in the reaction solution was 0.114% by weight for the benzamide compound and 0.002% by weight for the benzoic acid compound. The reaction temperature was maintained at 75° C., and the reaction product solution taken out of the reactor was analyzed by gas chromatography, showing that the yield of m-xylylenediamine was 87.8 mol %.

The reaction was continued by raising only the temperature so as to keep the above yield of m-xylylenediamine, thereby evaluating the catalyst life by the number of days taken until the reaction temperature for keeping the yield reached 90° C. After 12 days, the reaction temperature reached 90° C.

Comparative Example 5

The same procedure as in Example 5 was repeated except for using isophthalonitrile containing as impurities 12.0% by weight of 3-cyanobenzamide and 0.89% by weight of 3-cyanobenzoic acid as the starting phthalonitrile compound for the hydrogenation. The concentration in the reaction solution was 1.20% by weight for the benzamide compound and 0.089% by weight for the benzoic acid compound. The reaction temperature was maintained at 75° C., and the reaction product solution taken out of the reactor was analyzed by gas chromatography, showing that the yield of m-xylylenediamine was only 59 mol %. Although the reaction temperature was changed in the range of 75 to 100° C., the yield of m-xylylenediamine was improved only to 70.8 mol % at 92° C.

EXAMPLE 9

A commercially available activated carbon-supported palladium catalyst "PDC-3000" available from Toyo C.C.I. Co., Ltd. (supported palladium: 3% by weight) was activated by reduction with hydrogen. A 100-ml autoclave was successively charged with 3.0 g of the activated catalyst, 12.8 g of isophthalonitrile containing as impurities 0.12% by weight of 3-cyanobenzamide and 0.12% by weight of 3-cyanobenzoic acid, 37 g of liquid ammonia, and 0.1 g of sodium hydroxide. Then, hydrogen was introduced into the autoclave to increase the inner pressure to 20 MPa (gauge). The concentration in the reaction solution was 0.043% by weight for the benzamide compound and 0.043% by weight for the benzoic acid compound. The autoclave was shaken at 50° C. for 30 min. The gas chromatographic analysis on the reaction product solution showed that the conversion of isophthalonitrile was 99.0 mol %, the yields of 3-cyanobenzylamine was 76.0 mol %, and the yield of m-xylylenediamine was 8.4 mol %. The by-products were substantially high-boiling substances.

Comparative Example 6

A commercially available activated carbon-supported palladium catalyst "PDC-3000" available from Toyo C.C.I. Co., Ltd. (supported palladium: 3% by weight) was activated by reduction with hydrogen. A 100-ml autoclave was successively charged with 3.0 g of the activated catalyst, 12.8 g of isophthalonitrile containing as impurities 3.42% by weight of 3-cyanobenzamide and 0.24% by weight of 3-cyanobenzoic acid, 37 g of liquid ammonia, and 0.1 g of sodium hydroxide. Then, hydrogen was introduced into the autoclave to increase the inner pressure to 20 MPa (gauge). The concentration in the reaction solution was 0.877% by weight for the benzamide compound and 0.062% by weight for the benzoic acid compound. The autoclave was shaken at 50° C. for 30 min. The gas chromatographic analysis on the reaction product solution showed that the conversion of isophthalonitrile was 92.0 mol %, the yields of 3-cyanobenzylamine was 54.3 mol %, and the yield of m-xylylenediamine was 4.2 mol %. The by-products were substantially high-boiling substances.

As seen from the above Examples, in accordance with the present invention, xylylenediamine and/or cyanobenzylamine are stably and economically produced at high yields with prolonged catalyst life by the hydrogenation of the phthalonitrile compound. Accordingly, the present invention is of great industrial value.

What is claimed is:

1. A process for producing xylylenediamine and/or cyanobenzylamine by a liquid-phase hydrogenation of a phthalonitrile compound in the presence of a catalyst, the liquid-phase hydrogenation being performed while controlling a concentration of a benzamide compound in a reaction solution to 0.35% by weight or lower, and wherein the hydrogenation is performed while further controlling a concentration of a benzoic acid compound in the reaction solution to 0.1% by weight or lower.

2. The process according to claim 1, wherein the concentration of the benzamide compound in the reaction solution is 0.07% by weight or lower.

3. The process according to claim 1, wherein the hydrogenation is performed while further controlling a concentration of a benzoic acid compound in the reaction solution to 0.05% by weight or lower.

4. The process according to claim 1, wherein the benzamide compound is at least one compound selected from the group consisting of 3-cyanobenzamide, 4-cyanobenzamide, isophthalamide, m-toluamide, p-toluamide and benzamide.

5. The process according to claim 1, wherein the benzoic acid compound is at least one compound selected from the group consisting of 3-cyanobenzoic acid, 4-cyanobenzoic acid, 3-methylbenzoic acid, 4-methylbenzoic acid, benzoic acid and salts of the preceding compounds.

6. The process according to claim 3, wherein the benzoic acid compound is at least one compound selected from the group consisting of 3-cyanobenzoic acid, 4-cyanobenzoic acid, 3-methylbenzoic acid, 4-methylbenzoic acid, benzoic acid and salts of the preceding compounds.

7. The process according to claim 1, wherein said catalyst is selected from catalysts containing nickel, cobalt or palladium.

8. The process according to claim 1, wherein the benzamide compound and the benzoic acid compound are contained with a starting phthalonitrile compound used in the hydrogenation, and the concentration of the benzamide compound and the benzoic acid compound are controlled by controlling contents of the benzamide compound and the benzoic acid compound contained with said starting phthalonitrile compound.

9. The process according to claim 8, wherein the concentration of the benzamide compound and the benzoic acid compound is controlled by a purification treatment of said starting phthalonitrile compound.

10. The process according to claim 9, wherein said purification treatment is a distillation process.

* * * * *